United States Patent [19]

Tschunt

[11] 4,292,525

[45] Sep. 29, 1981

[54] DIAGNOSTIC RADIOLOGY APPARATUS FOR PRODUCING LAYER IMAGES OF AN EXAMINATION SUBJECT

[75] Inventor: Edgar Tschunt, Rathsberg, Fed. Rep. of Germany

[73] Assignee: Siemens Aktiengesellschaft, Berlin & Munich, Fed. Rep. of Germany

[21] Appl. No.: 68,230

[22] Filed: Aug. 20, 1979

[30] Foreign Application Priority Data

Sep. 20, 1978 [DE] Fed. Rep. of Germany ....... 2840965

[51] Int. Cl.³ .......................... A61B 6/00; G01T 1/20; H01J 35/16
[52] U.S. Cl. ................................. 250/445 T; 250/367; 250/508
[58] Field of Search ................... 250/508, 505, 445 T, 250/385, 367

[56] References Cited

U.S. PATENT DOCUMENTS

| | | | |
|---|---|---|---|
| 4,051,379 | 9/1977 | Zacher, Jr. | 250/385 |
| 4,055,767 | 10/1977 | Allemand | 250/385 |
| 4,070,581 | 1/1978 | Gibbons et al. | 250/367 |

Primary Examiner—Alfred E. Smith
Assistant Examiner—T. N. Grigsby
Attorney, Agent, or Firm—Hill, Van Santen, Steadman, Chiara & Simpson

[57] ABSTRACT

In an exemplary embodiment, a measuring arrangement comprises a radiation source emitting a radiation beam which penetrates the body layer to be examined, and a radiation receiver which supplies electrical output signals corresponding to the radiation intensity measured, a computer being connected with the radiation receiver for computing from the output signals of the radiation receiver the attenuation values of specific image points of the body layer. There is a collimator with a collimator grid forming a shielding compartment for each detector. Each detector is arranged in its collimator grid compartment and can be secured to a plate forming part of the grid, the plate being removably inserted in two parallel side portions forming the sides of each grid compartment. Furthermore, each plate with the detector secured thereto can project slightly beyond the radiation exit side of the side portions, so that a simple electrical connection to the detectors is possible.

5 Claims, 6 Drawing Figures

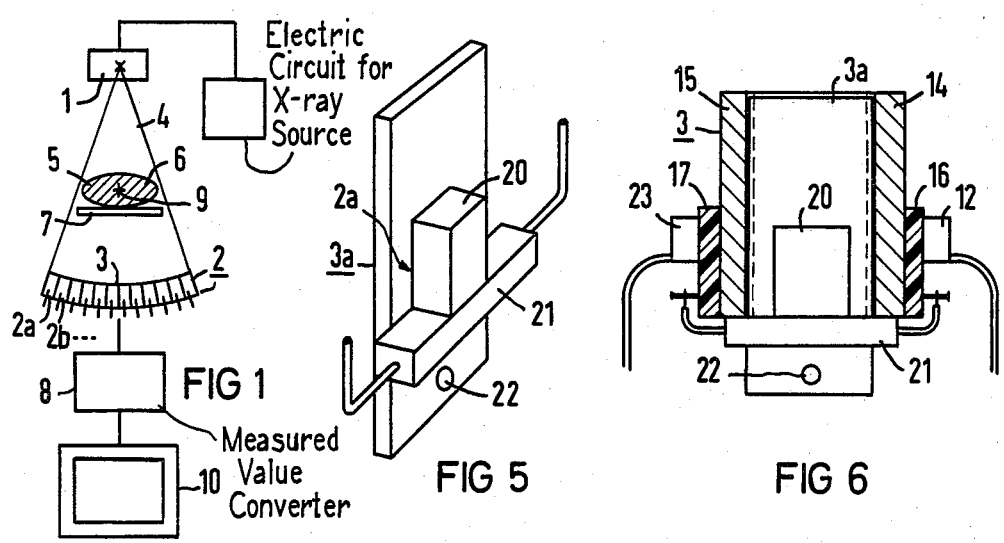
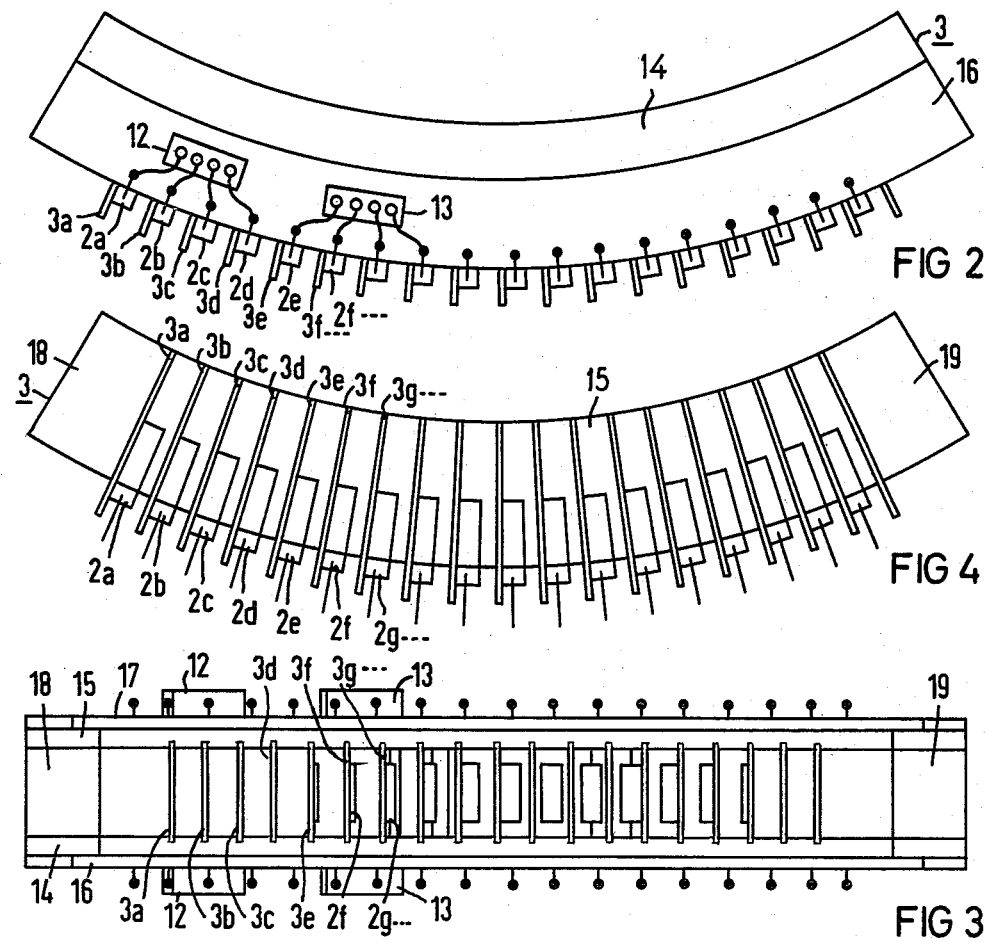

DIAGNOSTIC RADIOLOGY APPARATUS FOR PRODUCING LAYER IMAGES OF AN EXAMINATION SUBJECT

BACKGROUND OF THE INVENTION

The invention relates to a diagnostic radiology apparatus for producing layer images of an examination subject, with a patient support, with a measuring arrangement for irradiating the examination subject from various directions, including a radiation source emitting a radiation beam which penetrates the layer to be examined, its dimension perpendicular to the layer plane being equal to the layer thickness, and of a radiation receiver which supplies electrical output signals corresponding to the radiation intensity measured, and with a computer connected with the radiation receiver for computing from the output signals of the radiation receiver the attenuation values of specific image points of the body layer penetrated by rays, wherein the radiation receiver comprises a row of detectors and for each detector there is a collimator.

With known diagnostic radiology apparatus of this kind, so-called computer-tomographs, the measuring arrangement is rotated, if necessary in several steps, lateral displacement of the measuring arrangement being effected between each rotational step for the purpose of scanning the complete layer to be examined of the examination subject, with the result that each radiation path in the layer examined is intersected by a plurality of other radiation paths and an image of the layer examined can be computed by the computer from the output signals of the radiation receiver. It is known in this connection to arrange the collimator at a location in front of the radiation receiver, so that the individual detectors of the radiation receiver are themselves no longer separated from one another by the collimator walls. As a result, however, it is possible for undesirable scattered radiation to act on the detectors. Furthermore, a separate support-mounting device is required for the detectors, which makes it difficult for detectors to be replaced individually.

SUMMARY OF THE INVENTION

The object underlying the invention is to construct a diagnostic radiology apparatus of the kind previously mentioned such that optimum protection of the detectors of the radiation receiver from scattered radiation is afforded and it is possible for individual detectors to be replaced with ease.

This object is achieved according to the invention in that each detector is arranged at least partially in a compartment of a collimator grid associated therewith. With the diagnostic radiology apparatus according to the invention the walls of the collimator grid shield the detectors from lateral, scattered radiation in an optimum manner. Furthermore, it is possible to replace individual detectors with ease by removing them from the corresponding collimator grid compartment.

It is particularly advantageous if the collimator is constructed of two side portions of radiation-absorbing material, which are disposed in parallel with a space therebetween and which are curved about the focus and provided on their inner sides with grooves disposed opposite each other wherein plates of radiation-absorbing material are inserted such that they can be removed. In this instance each detector can be secured, preferably by adhesion, to a plate of its collimator grid section. An individual detector can be replaced in a simple manner by removing the plate to which it is secured from the collimator. If each collimator plate projects, with that part of its detector which has the connections, slightly in the direction of radiation beyond the radiation exit side of the side portions of the collimator, then a simple connection of the electric terminal elements of the detectors with the conductors coordinated thereto is possible, which conductors can be provided, for example, on printed circuit boards mounted on the exteriors of the side portions. The collimator plates likewise offer good protection against scattered radiation.

The invention is described in greater detail below with the aid of an exemplary embodiment represented in the accompanying sheet of drawing; and other objects, features and advantages will be apparent from this detailed disclosure and from the appended claims.

BRIEF DESCRIPTION OF THE DRAWING

FIG. 1 shows a schematic representation of a diagnostic radiology apparatus for illustrating the underlying conception of the invention;

FIG. 2 shows a somewhat diagrammatic elevational view of the radiation receiver with the collimator coordinated thereto in the apparatus according to FIG. 1;

FIG. 3 shows a top-plan view of the radiation receiver with the collimator according to FIG. 2;

FIG. 4 is a diagrammatic view similar to FIG. 2, but with a side portion removed to reveal interior parts; and FIGS. 5 and 6 show a detail of the radiation receiver and collimator according to FIGS. 2 to 4, FIG. 5 being a perspective view and FIG. 6 being a transverse sectional view.

DETAILED DESCRIPTION

In FIG. 1 an x-ray tube 1 is shown as radiation source, which with a radiation receiver 2 forms a measuring arrangement. The radiation receiver 2 comprises a row of detectors 2a, 2b, etc., each of which is partially arranged in the grid formed by a collimator 3. The x-ray tube 1 is fixedly connected with the radiation receiver 2 and the collimator 3 via a rotating frame. The x-ray tube 1 emits an x-ray beam 4 in the form of a fan, its extent in the transverse layer 5 to be examined of a patient 6 located on a patient support 7 being such that the entire layer 5 to be examined is penetrated by x-radiation. The dimension of the x-ray beam 4 perpendicular to the layer 5 is equal to the layer thickness. The number of detectors of the radiation receiver 2 is selected according to the desired image resolution and can be, for example, 512. Each detector supplies a signal corresponding to the intensity of the x-radiation received. The detectors of the radiation receiver 2 are connected with a computer or measured value converter 8 which computes the attenuation values of specific image points of the layer 5 and hence an image of the layer 5 penetrated by rays from the output signals of the detectors, which are produced while the measuring arrangement 1, 2 rotates through an angle of 360° about the axix of rotation 9. This image is reproduced on a monitor 10. In order to reduce the radiation to which the patient 6 is exposed, the x-ray tube 1 can be pulsed during a scanning operation with the result that, for example, one set of output signals of the radiation receiver 2 is produced per degree of angle. For example, 360×512 output signals are produced in this way. For the sake of clarity, not all the detectors are shown in the example, but only a small number of detectors.

It can be seen from FIG. 2 that the collimator has plates 3a, 3b, etc., which on the radiation exit side of the collimator 3 project downward slightly beyond two side portions such as 14 (described in greater detail in conjunction with FIGS. 3, 4, and 6). Each of the collimator plates 3a, etc., bears a detector which likewise projects downwards slightly beyond the side portions of the collimator 3, with the result that according to FIG. 2 the connections or electric terminal elements of each detector are exposed and can easily be connected with the corresponding conductors of a printed circuit board secured to each side portion such as 14 on its exterior. Each detector 2a, etc., is thus partially arranged in the compartment of the collimator grid coordinated thereto. The printed circuit board 16 is shown in FIG. 2. The connection can be made by soldering. According to FIG. 2, on the printed circuit board 16 four detector connections are guided to one connector respectively, of which the connectors 12 and 13 are shown. The same also applies to the connections of the detectors, which are not visible in FIG. 2, and the corresponding printed circuit board (17 FIG. 6) on the non-visible side of the collimator 3.

FIG. 3 shows a top-plan view of the collimator 3 with the detectors such as 2f and 2g being partially visible. The two side portions 14 and 15 and also the printed circuit boards 16 and 17 are visible here. At the ends, the collimator 3 is held between two blocks 18, 19 which determine the distance between the side portions 14, 15. The plates 3a, etc., which consist of radiation-absorbing material, for example of tantalum, are inserted such that they can be removed in grooves or slits in the side portions 14, 15 which are likewise of radiation-absorbing material. The plates 3a, etc., can thus be removed individually from the collimator 3 on the radiation exit side thereof. It is thereby possible to replace an individual detector with ease by removing the plate to which the detector is attached preferably by adhesion.

The side portions 14, 15 can be composed, for example, of casting resin mixed with lead powder.

FIG. 4 shows a section through the collimator 3 (side portion 14 being removed). In this it is clearly recognizable that the predominant part of the detectors 2a, etc., is located within the compartments of the grid of the collimator 3, whereas only the part of the detectors 2a, etc., which bears the connections or electric terminal elements projects on the radiation exit side of the collimator 3, with the result that the detectors 2a, etc., can be easily connected to the printed circuit boards 16, 17. Furthermore, it is apparent from FIG. 4 that the plates 3a, etc., likewise project on the radiation exit side of the collimator 3; namely, project slightly beyond the radiation exit sides of the side portions 14, 15, with the result that the plates 3a, etc., shield the detectors 2a, etc., successfully from scattered radiation.

FIG. 5 shows a single collimator plate 3a with the detector 2a secured thereto. The detector consists of a scintillating crystal 20 and of a photoelectric transducer 21, for example a photodiode, which is connected to the scintillating crystal 20. The scintillating crystal 20 can be enclosed on all sides in a lightproof manner with the exception of its side connected with the photoelectric transducer 21. Each collimator plate 3a, etc., bears a detector in accordance with the construction shown in FIG. 5. Each plate is also provided with an aperture allowing extraction from the side portions 14, 15 and hence from the collimator for the purpose of replacing the detector. FIG. 5 shows the aperture 22 of the collimator plate 3a. All the scintillating crystals receiving the x-radiation are thus completely located within the respective compartments of the collimator grid coordinated thereto.

FIG. 6 shows a cross section through the collimator 3 with the side portions 14, 15, the printed circuit boards 16, 17 and also the connector devices 12 and 23 mounted thereon. For example, the plate 3a bearing the scintillating crystal 20 with the photoelectric transducer 21 is visible between the side portions 14, 15. Flat-strip cables can lead from the connector devices 12, 23, etc., to the actual measuring electronics of measured value converter 8. The side portions 14, 15, their distance apart being determined by the blocks 18, 19, and which are disposed in parallel with one another, are curved about the focus of the x-ray tube 1.

The invention is not limited to application with a computer-tomograph having a radiation receiver which can be rotated continuously or in step-by-step fashion, but is also applicable if the radiation receiver is constructed as a ring which encloses the examination subject and which is stationary during scanning, thus with which only the radiation beam is rotated as the examination subject is scanned.

It will be apparent that many modifications and variations may be effected without departing from the scope of the novel concepts and teachings of the present invention.

I claim as my invention:

1. In a diagnostic radiology apparatus for producing layer images of an examination subject with a patient support, a measuring arrangement for irradiating the examination subject from various directions including a radiation source adapted to emit a radiation beam which penetrates the layer to be examined, a radiation receiver which supplies electrical output signals corresponding to the radiation intensity measured, and a measured value converter connected with the radiation receiver for computing from the output signals of the radiation receiver attenuation values of specific image points of the irradiated body layer, an improvement to the radiation receiver comprising:

a collimator grid formed with a plurality of spaced apart compartments with a detector located at least partly in each said compartment, each said detector comprises a scintillating crystal with an optical output and an associated photoelectric transducer adapted to sense light emitted from said optical output, each said crystal and said associated photoelectric transducer are attached to a selected wall of a respective collimator compartment whereby each said crystal, said associated photoelectric transducer and said wall form a unit.

2. A diagnostic radiology apparatus for producing layer images of an examination subject, with a patient support, a measuring arrangement for irradiating the examination subject from various directions, comprising a radiation source emitting a radiation beam which penetrates the layer to be examined, its dimension perpendicular to the layer plane being substantially equal to the layer thickness, and a radiation receiver which supplies electrical output signals corresponding to the radiation intensity measured, and a measured value converter connected with the radiation receiver for computing from the output signals of the radiation receiver the attenuation values of specific image points of the irradiated body layer, the radiation receiver comprising a row of detectors, and a collimator for each detector, characterized in that the collimator comprises a collimator grid with a compartment for each detector (2a, etc.), each detector being at least partially in the collimator grid compartment associated therewith, and characterized in that the collimator (3) has two side portions (14, 15) of radiation-absorbing material disposed in parallel with a space therebetween, said side portions being curved about the radiation source and being provided on their inner sides with slits disposed opposite each other, and plates (3a, etc.) of radiation-absorbing material inserted in said slits such that they can be removed.

3. A diagnostic radiology apparatus according to claim 2, characterized in that each detector (2a, etc.) is secured, to one of said plates (3a, etc.), said plate defining a wall of the associated collimator grid compartment.

4. A diagnostic radiology apparatus for producing layer images of an examination subject, with a patient support, a measuring arrangement for irradiating the examination subject from various directions, comprising a radiation source emitting a radiation beam which penetrates the layer to be examined, its dimension perpendicular to the layer plane being substantially equal to the layer thickness, and a radiation receiver which supplies electrical output signals corresponding to the radiation intensity measured, and a measured value converter connected with the radiation receiver for computing from the output signals of the radiation receiver the attenuation values of specific image points of the irradiated body layer, the radiation receiver comprising a row of detectors, and a collimator for each detector, characterized in that the collimator comprises a collimator grid with a compartment for each detector (2a, etc.), each detector being at least partially in the collimator grid compartment associated therewith, and characterized in that each detector (e.g. 2a) is composed of a scintillating crystal (e.g. 20) having an optical output and of a photoelectric transducer (e.g. 21) connected to said optical output, and the scintillating crystal (20) being disposed within the associated collimator grid compartment, each collimator grid comprises a collimator plate (3a, etc.) with the photoelectric transducer (e.g. 21) thereon and both projecting in the radiation direction slightly beyond the radiation exit side of the collimator grid.

5. A diagnostic radiology apparatus according to claim 4, characterized in that the collimator has two side portions (14, 15) of radiation-absorbing material disposed in parallel and defining the sides of each collimator grid, the collimator plates (3a, etc.) projecting in the radiation direction slightly beyond said side portions, and the photoelectric transducers (e.g. 21) being disposed below the side portions, printed circuit boards (16, 17) being mounted on the exteriors of the side portions (14, 15), and the photoelectric transducers being connected to said printed circuit boards.

* * * * *